«  » 
United States Patent [19]

Patel et al.

[11] Patent Number: 5,081,040
[45] Date of Patent: Jan. 14, 1992

[54] COMPOSITION AND KIT FOR TESTING FOR OCCULT BLOOD IN HUMAN AND ANIMAL EXCRETIONS, FLUIDS, OR TISSUE MATRIXES

[75] Inventors: Chandravadan Patel, Laguna Niguel; Jangbir S. Sangha, Laguna Hills, both of Calif.

[73] Assignee: Helena Laboratories Corporation, Beaumont, Tex.

[21] Appl. No.: 363,457

[22] Filed: Jun. 6, 1989

Related U.S. Application Data

[63] Continuation of Ser. No. 68,745, Jun. 29, 1987, abandoned, which is a continuation of Ser. No. 888,240, Jul. 21, 1986, abandoned.

[51] Int. Cl.$^5$ .................... G01N 21/78; G01N 33/72
[52] U.S. Cl. ........................ 436/66; 422/56; 422/57; 422/61; 435/28; 435/805; 436/169
[58] Field of Search ................... 436/66, 169; 422/56–58, 61; 435/28, 805; 427/2

[56] References Cited

U.S. PATENT DOCUMENTS

| | | |
|---|---|---|
| Re. 28,575 | 10/1975 | Bauer . |
| 2,223,520 | 12/1940 | Ioannu . |
| 2,290,436 | 7/1942 | Kamlet . |
| 2,387,244 | 10/1945 | Compton et al. . |
| 2,394,140 | 2/1946 | Biscow . |
| 2,418,392 | 4/1947 | Bender . |
| 2,567,445 | 9/1951 | Parker . |
| 2,754,289 | 7/1956 | Meyer . |
| 2,773,906 | 12/1956 | Emerson . |
| 2,799,660 | 7/1957 | Nicholls et al. . |
| 2,800,457 | 7/1957 | Green et al. . |
| 2,800,458 | 7/1957 | Green . |
| 2,823,984 | 2/1958 | Mavrodineanu . |
| 2,838,377 | 6/1958 | Fonner . |
| 2,848,308 | 8/1958 | Free . |
| 2,886,445 | 5/1959 | Rosenthal et al. . |
| 2,893,844 | 7/1959 | Cook ............................ 435/805 X |
| 2,905,594 | 9/1959 | Morris . |
| 2,930,695 | 3/1960 | Rosner et al. . |
| 2,953,454 | 9/1960 | Berman . |
| 2,986,453 | 5/1961 | Collins . |
| 3,012,976 | 12/1961 | Adams, Jr. et al. . |
| 3,017,879 | 1/1962 | Sapit et al. . |
| 3,034,922 | 5/1962 | Boë et al. . |
| 3,042,496 | 7/1962 | Fancher et al. . |
| 3,043,782 | 7/1962 | Jensen . |
| 3,057,723 | 10/1962 | Jeffreys et al. . |
| 3,066,081 | 11/1962 | Rorem et al. . |
| 3,092,463 | 6/1963 | Adams, Jr. et al. . |
| 3,092,464 | 6/1963 | Adams, Jr. et al. . |
| 3,116,223 | 12/1963 | Rosner et al. . |
| 3,183,173 | 5/1965 | Oakes . |
| 3,232,710 | 2/1966 | Rieckmann et al. . |
| 3,252,762 | 5/1966 | Adams, Jr. et al. . |
| 3,290,117 | 12/1966 | Adams, Jr. et al. . |
| 3,293,683 | 12/1966 | Wyant . |
| 3,350,278 | 10/1967 | Gretton et al. . |
| 3,406,015 | 10/1968 | Foster . |
| 3,406,106 | 10/1968 | Garwood et al. . |

(List continued on next page.)

*Primary Examiner*—Robert J. Hill, Jr.
*Attorney, Agent, or Firm*—Spencer & Frank

[57] ABSTRACT

A diagnostic kit is disclosed for the detection of hemoglobin, myoglobin, ferritin, or the like substances having peroxidase-like activity in different mixtures of biological origin, such as fecal blood in toilet bowl, occult blood in the breath of internally bleeding horses, or myoglobin in the urine of severely muscle damaged victims. The kit includes, in an air, moisture, and light proof package, an inert water insoluble matrix, such as a sheet of paper, which has an area where a chemical composition containing a water soluble polymer, or polymers, is deposited in at least two separate steps of thin film coating, for the detection of the above substances. The composition further includes one or more oxygen donors, one or more organic peroxides or other suitable oxidizing agents, and a leuco-dye which gives a colored oxidation product when it is oxidized by the oxidizing agents with the hemoglobin or like substance acting as the catalyst. Also disclosed is a method of making the test device for use in the kit. Also disclosed is a method of making the test device for use in the kit.

20 Claims, 3 Drawing Sheets

U.S. PATENT DOCUMENTS

| | | | |
|---|---|---|---|
| 3,411,887 | 11/1968 | Ku . | |
| 3,418,079 | 12/1968 | Rey et al. . | |
| 3,438,737 | 4/1969 | Atkinson et al. . | |
| 3,443,903 | 5/1969 | Haack et al. . | |
| 3,447,536 | 6/1969 | Snyder . | |
| 3,453,180 | 7/1969 | Fraser, Jr. et al. . | |
| 3,466,145 | 9/1969 | Van Duyne . | |
| 3,472,738 | 10/1969 | Foster . | |
| 3,507,269 | 4/1970 | Berry . | |
| 3,509,872 | 5/1970 | Truhan . | |
| 3,511,608 | 5/1970 | Anderson . | |
| 3,526,480 | 9/1970 | Findl et al. . | |
| 3,552,925 | 1/1971 | Fetter . | |
| 3,558,435 | 1/1971 | Rey et al. . | |
| 3,598,704 | 8/1971 | Dahlqvist . | |
| 3,625,654 | 12/1971 | Van Duyne . | |
| 3,627,697 | 12/1971 | Rey et al. . | |
| 3,627,698 | 12/1971 | Rey et al. . | |
| 3,630,847 | 12/1971 | Rey et al. . | |
| 3,630,957 | 12/1971 | Rey et al. . | |
| 3,654,179 | 4/1972 | Bauer . | |
| 3,654,180 | 4/1972 | Bauer . | |
| 3,668,076 | 6/1972 | Rey et al. . | |
| 3,672,351 | 6/1972 | Ubersax et al. . | |
| 3,699,005 | 10/1972 | Foster . | |
| 3,712,853 | 1/1973 | Rittersdorf et al. . | |
| 3,713,772 | 1/1973 | Tavel . | |
| 3,811,840 | 5/1974 | Bauer et al. . | |
| 3,814,668 | 6/1974 | Blake et al. . | |
| 3,847,553 | 11/1974 | Verbeck . | |
| 3,853,468 | 12/1974 | Haymond . | |
| 3,853,471 | 12/1974 | Rittersdorf et al. . | |
| 3,853,472 | 12/1974 | Rittersdorf et al. . | |
| 3,854,885 | 12/1974 | Fromm et al. . | |
| 3,912,457 | 10/1975 | Ogawa et al. . | |
| 3,917,452 | 11/1975 | Rittersdorf et al. . | |
| 3,964,871 | 6/1976 | Hochstrasser | 435/805 X |
| 3,975,161 | 8/1976 | Svoboda et al. | 436/66 X |
| 3,986,833 | 10/1976 | Mast et al. | 436/66 |
| 3,996,006 | 12/1976 | Pagano . | |
| 4,005,984 | 2/1977 | Alsop . | |
| 4,017,261 | 4/1977 | Svoboda et al. | 436/66 X |
| 4,035,150 | 7/1977 | Jaffe | 436/66 |
| 4,046,514 | 9/1977 | Johnston et al. | 436/66 X |
| 4,061,468 | 12/1977 | Lange et al. . | |
| 4,063,894 | 12/1977 | Ogawa et al. . | |
| 4,071,318 | 1/1978 | Lam . | |
| 4,092,120 | 5/1978 | Suovaniemi et al. . | |
| 4,148,611 | 4/1979 | Nand et al. . | |
| 4,175,923 | 11/1979 | Friend . | |
| 4,219,336 | 8/1980 | Guthlein et al. . | |
| 4,220,713 | 9/1980 | Rittersdorf et al. | 436/66 X |
| 4,251,222 | 2/1981 | White . | |
| 4,251,223 | 2/1981 | White . | |
| 4,260,393 | 4/1981 | Gibson . | |
| 4,269,938 | 5/1981 | Frank . | |
| 4,277,250 | 7/1981 | Melnick et al. . | |
| 4,278,439 | 7/1981 | White | 436/66 |
| 4,292,272 | 9/1981 | Kitajima et al. . | |
| 4,303,409 | 12/1981 | Ogawa et al. . | |
| 4,310,626 | 1/1982 | Burkhardt et al. | 436/66 X |
| 4,329,317 | 5/1982 | Detweiler et al. . | |
| 4,333,734 | 6/1982 | Fleisher . | |
| 4,365,970 | 12/1982 | Laurence et al. . | |
| 4,385,114 | 5/1983 | Guthlein et al. | 435/805 X |
| 4,447,542 | 5/1984 | Gantzer | 436/66 |
| 4,486,536 | 12/1984 | Baker et al. | 436/66 |
| 4,493,892 | 1/1985 | Fleisher . | |
| 4,511,533 | 4/1985 | Guadagno et al. . | |
| 4,541,987 | 9/1985 | Guadagno . | |
| 4,556,640 | 12/1985 | Gantzer | 436/66 |
| 4,578,358 | 3/1986 | Oksman et al. . | |
| 4,725,553 | 2/1988 | Guadagno . | |
| 4,742,002 | 5/1988 | Guadagno . | |

FOREIGN PATENT DOCUMENTS 0093595 11/1983 European Pat. Off. .

OTHER PUBLICATIONS

Svoboda et al., *Chemical Abstracts*, vol. 85, Abs. No. 85:30353g (1976), p. 186.

COMPOSITION AND KIT FOR TESTING FOR OCCULT BLOOD IN HUMAN AND ANIMAL EXCRETIONS, FLUIDS, OR TISSUE MATRIXES

CROSS-REFERENCE TO RELATED APPLICATIONS

This Application is a continuation of application Ser. No. 07/068,745 filed June 29th, 1987, now abandoned, which is a Continuation of application Ser. No. 06/888,240 filed July 21st, 1986, now abandoned.

BACKGROUND OF THE INVENTION

The present invention is in the field of diagnostic kits. More particularly, the present invention is directed to diagnostic kits for detection of hemoglobin, myoglobin, ferritin, or the like substances having peroxidase-like activity in different mixtures of biological origin, such as fecal blood in a toilet bowl, occult blood in the breath of bleeding horses, or myoglobin present in the urine of severely muscle damaged victims.

Techniques based on a visually observable color reaction for detecting the presence of occult blood in biological specimens, such as human feces and urine, have been known for a long time in the clinical diagnostic and related arts.

A basic description of such a test for occult blood is given, for example, in the book 37 A SYLLABUS OF LABORATORY EXAMINATIONS IN CLINICAL DIAGNOSIS", Harvard University Press, Cambridge, Mass., 1966, L. B. Page and P. J. Culver, Editors, pages 377-478.

Briefly, this well known test takes advantage of the peroxidase activity of hemoglobin, whereby hemoglobin catalyzes the decomposition of hydrogen peroxide ($H_2O_2$), or of several other peroxide compounds into water and 37 nascent" oxygen (37 O"). The resulting "nascent" oxygen reacts with gum guaiac, containing phenol guaiacetic acid giving rise to a colored dye reaction product having a quinone-type structure. In its simplest form, described, for example, in the above-noted reference book, a small sample of the stool to be tested is applied to the filter paper and a few drops of glacial acetic acid, of saturated ethanolic gum guaiac solution, and of three percent (3%) aqueous hydrogen peroxide solution, are added. The appearance of a blue or bluish green color indicates the presence of peroxidase-like activity, and, therefore, the presence of occult blood in the stool sample.

Many variations of the above-summarized basic test procedure, in terms of the chemicals and/or apparatus employed, were developed in the art, as is apparent from the following patents and other references: U.S. Pat. No. 4,427,769; U.S. Pat. No. 4,092,120; U.S. Pat. No. 4,472,498; U.S. Pat. No. 4,016,043; U.S. Pat. No. 4,436,823; U.S. Pat. No. 4,333,734; "Spectrophotometry of Occult Blood In Feces", *Clin-Chem* 1983, Dec. 29(12), pages 2022-2025, by C. L. Welch, et al.; "Occult Fecal Blood Loss Determined By Chemical Tests and A 51 Cr Method", *Scand. Journal of Gastroenterology*, 1981, 16(2), pages 245-252, by J. H. Dybdahl, et al.; "A New Occult Blood Test Not Subject To False-Negative Results from Reducing Substances", *J. Lab. Clin. Med.*, 1979, May 93(5), pages 879-886, by R. M. Jaffe, et al.; "HemoQuant, A New Quantitative Assay For Fecal Hemoglobin", *Ann. Intern. Med.*, 1984, September 101(3), pages 297-302, by D. A. Ahiquist, et al.; "Detection of Occult Blood In Gastric Juice", *Journal of Clinical Gastroenterology*, 1984, April 6(2), pages 119-121, by P. Rosenthal, et al.; "Screening For Colorectal Cancer Using Guaiac Slide Test", the Hemocult II Stool Guaiac Slide Test", *Cancer*, 1984, May 53(10), pages 2201-2205, by K. M. Cummings, et al.; "The Use of Hemocult Test For Detection of Blood In Gastric Aspirates", *Scand. Journal of Gastroenterology*, 1983, 18(6), pages 723-727, by M. Starlinger, et al.; "The Hemomatic Analyzer: A New Occult Blood Testing Device", *American Journal of Gastroenterology*, 1984, February 79(2), pages 117-121, by D. Y. Graham, et al.; "The Early Detection of Colorectal Cancer", *Cancer*, 1977, August 40(2), pages 945-949, by S. F. Miller, et al.; "Reliability of Chemical Tests For Fecal Occult Blood In Hospitalized Patients", *American Journal of Digestive Diseases, October*, 1976, 21(10), pages 845-852, by D. W. Morris, et al.; and "Tests For Occult Blood In Stools of Children", *Arch. Dis. Child.*, March, 1975, 50(3), pages 238-240, by A. E. Ford-Jones, et al.

As the above-cited references demonstrate, testing for occult blood in human stool samples provides a very significant aid to the early detection, and therefore early treatment of colorectal cancer In addition to gum guaiac, other chromogenic substances have also been used in the prior art to provide a visually observable colored dye to indicate the presence of occult blood (or better stated, peroxidase activity) in stool samples and other biological specimens. These chromogens include, for example, orthotolidine, phenolphthalein, and tetramethylbenzidine, although gum guaiac still appears to be the chromogen employed in most tests.

One problem which arises in connection with the occult blood tests of the prior art relates primarily to the sensitivity of the tests. The test should be neither too sensitive so as to give false positive results, nor less than adequately sensitive to give false negative results. Generally speaking, the prior art attempted to solve this problem by mixing the chromogenic agent or agents with certain reducing agents so as to provide the "right" sensitivity to the overall chemical composition used in the tests.

Another problem, which arises in connection with occult blood tests in fecal samples, relates to the manner of handling and processing the aesthetically undesirable specimens. As is evident from the above-cited patents, the prior art attempted to render the handling of stool samples less disagreeable in the laboratory phase of the testing process by providing various sample receiving and storing apparatus.

Still another development in the prior art regarding tests for occult blood in human feces or urine is represented by a test kit sold by Helena Laboratories Corporation of Beaumont, Texas under the CS-T trademark. This test kit comprises a solid testing powder composition containing guaiac derivative as the chromogen, enclosed between two sheets of paper, substantially as is schematically shown on FIGS. 1 and 2 (labeled as "PRIOR ART") of the appended drawings. The kit contains several "bags" or "pouches" of the testing powder composition, and also two bags or pouches of "control" samples, one positive and the other negative, of a second and third powder composition, which is designed to provide color and no color reaction respectively even in the presence or absence of occult blood. The CS-T test kit is usable for "self-testing" by a lay person for detection of occult blood in the stool or urine, by placing the kit into the toilet bowl after a bowel movement. There, the test chemicals located between the two sheets of paper react, in the presence of hemoglobin, to develop an intense color in the test areas where the reactive powder is located.

The present invention represents a still further development in the technological field of test kits for occult blood, particularly of the type which is readily usable by a lay person in a "self-testing" process.

SUMMARY OF THE INVENTION

It is an object of the present invention to provide a diagnostic composition for detecting the presence in an aqueous solution of a substance having peroxidase-like activity.

It is another object of the present invention to provide a test kit for detecting the presence of occult blood in human waste samples, such as stool or urine samples, which kit is readily usable by a lay person without disagreeable manipulation of the samples.

It is yet another object of the present invention to provide a test kit for detecting the presence of occult blood in human waste samples, which kit provides clear, unambiguous indication of positive results to a lay user.

It is yet another object of the present invention to provide a test kit for detecting the presence of occult blood in human waste samples, which kit is relatively inexpensive to manufacture.

It is yet another object of the present invention to provide a test kit for detecting the presence of occult blood in human waste samples, which kit is substantially biodegradable.

It is yet another object of the present invention to provide a method of preparing a test device for detecting the presence of occult blood in human waste samples.

The foregoing and other objects and advantages are attained by a test kit having an inert water insoluble matrix, such as a sheet of biodegradable paper, and a chemical composition embedded in an area in the matrix and immobilized in a water soluble polymer, such as polyvinylpyrrolidone. The chemical composition is adapted for providing a visually observable color reaction in the presence of approximately 1.5 to 2.0 mg of hemoglobin (or like substance having peroxidase-like activity) per 100 ml of the aqueous system in which the test kit is used. To this end, the chemical composition includes one or more oxygen donors, such as one or more organic peroxides, and may include a buffer of pH approximately 4 to 6.

In the preferred embodiment of the test kit of the present invention, the area containing the chemical composition is configured in the shape of a plus sign, and the chemical composition, including the water soluble polymer or polymers, is deposited on the matrix by a printing process.

The features of the present invention, together with further objects and advantages, can be best understood by reference to the following description, taken together with the appended drawings.

DESCRIPTION OF THE PREFERRED EMBODIMENT

Figure 1:
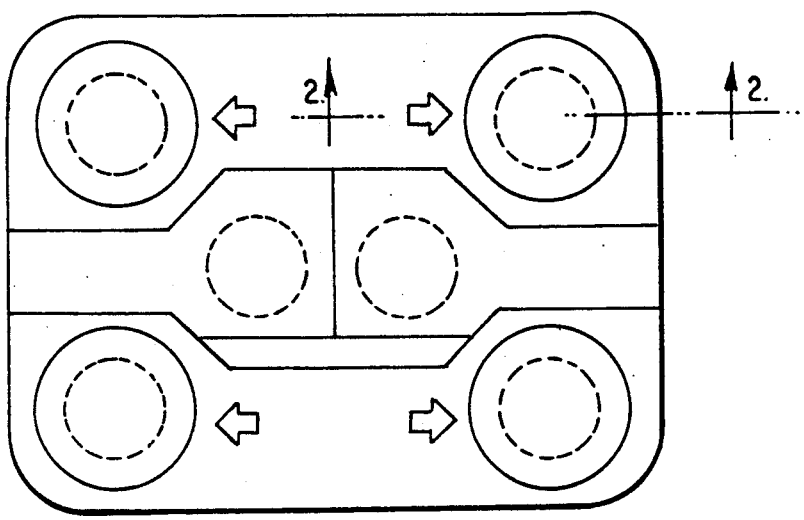
FIG. 1 is a schematic top view of a test kit used in the prior art for detecting the presence of occult blood in an aqueous system, such as a toilet bowl, which also contains a stool sample.
Figure 2:
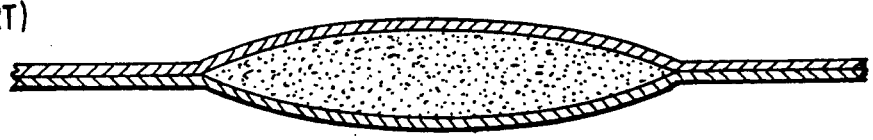
FIG. 2 is a schematic cross-sectional view of the prior art test kit, the cross-section being taken along lines 2,2 of FIG. 1.
Figure 3:
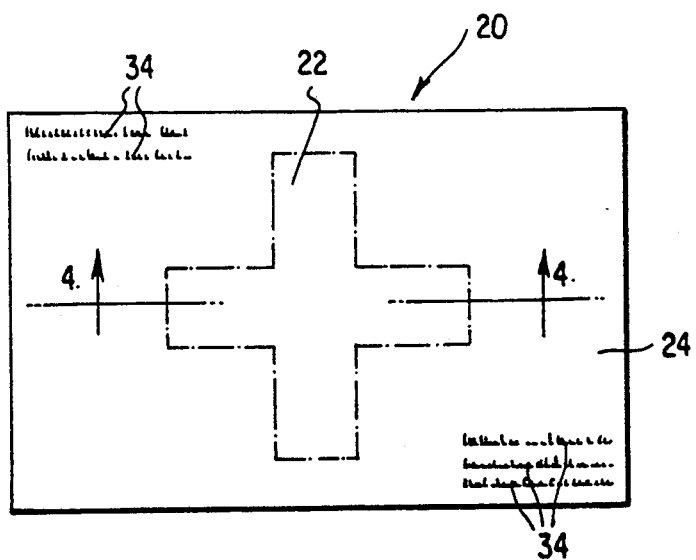
FIG. 3 is a schematic top view of a preferred embodiment of the test kit of the present invention.
Figure 4:
FIG. 4 is a cross-sectional view of the preferred embodiment of the test kit of the present invention, the cross-section being taken along lines 4,4 of FIG. 3.

The following specification taken in conjunction with the drawings sets forth the preferred embodiment of the present invention. The embodiment of the invention disclosed herein is the best mode contemplated by the inventors for carrying out their invention in a commercial environment, although it should be understood that several modifications can be accomplished within the scope of the present invention.

A test kit 20 is provided in accordance with the present invention, in which a distinct area 22 in a matrix of a sheet 24 of paper, or like water insoluble material having fibers or interstitial spaces, contains a chemical composition adapted for detecting the presence of hemoglobin, myoglobin, ferritin, or the like substances, having peroxidase-like activity.

More particularly, in one embodiment of the test kit 20 of the present invention there is provided a sheet of paper of approximately 3.25"×3.25" square, which has the above-mentioned chemical composition applied, preferably film coated, in an area 22 configured in the shape of a plus sign (+). Although the nature of the paper is not critical, the paper is preferably of the "short fiber" type, which is substantially water repellant, so it does not wet readily when it is dipped into an aqueous system. The paper is preferably also biodegradable.

The chemical composition, which is deposited and immobilized in the distinct area 22 of the paper sheet 24, includes one or more chromogenic substances of the type which undergo a color change as a result of oxidation with hydrogen peroxide, organic peroxides, inorganic persulfates, or like oxidizing agents in the presence of hemoglobin, myoglobin, ferritin, or the like substances having peroxidase-like activity. Examples of suitable chromogens are 3,3',5,5'-tetramethylbenzidine, substituted phenols, guaiac, guaiac derivatives, 4-chloronaphthol, aromatic amines, 2,7-diaminofluorene, orthotolidine, orthophenylenediamine, luminol, and acid fuchsin.

The chemical composition further includes one or more of the above-noted oxidizing agents, or sources, for "nascent" oxygen. Specific examples of suitable oxidizing agents are: $\alpha,\alpha'$-dimethylbenzoyl peroxide, other alkyl and aromatic and inorganic peroxides, urea hydroperoxide (also known under the tradename ORTIZONE), hydrogen peroxide ($H_2O_2$), ammonium persulfate [$(NH_4)_2S_2O_8$], potassium persulfate ($K_2S_2O_8$), certain transitional metal salts and certain oxidizing agents such as chlorinated heterocyclic derivatives.

Still further, the chemical composition may include a suitable buffer of approximately pH 4 to 6, such as a citrate or acetate buffer, and one or more reducing agents, such as ascorbic acid or a quinoline derivative. The function of the buffer in the composition will be readily understood by those skilled in the art. The function of the reducing agents is to "modulate" the sensitivity of the test, and to prevent a color reaction from occurring during manufacture and storage.

A suitable surface active agent (surfactant) which may be ionic, non-ionic, or amphoteric in nature may also be included in the composition. More than one surface active agent may be used.

A critical ingredient of the composition used in the test kit of the present invention comprises one or more water soluble polymers which are present in substantial amounts, say more than approximately 5%–60%, of the weight of the composition. The water soluble polymer or polymers serve the function of film coating and immobilizing the other ingredients in the matrix of the paper sheet 24, so that the ingredients are relatively stable, and do not react with one another until the test kit 20 is dipped into an aqueous system (not shown) for the purpose of performing the test. The water soluble polymers used in the present invention preferably are solid or semi-solid materials at room temperature. Examples of suitable polymers are polyvinylpyrrolidone, polyvinyl alcohol, polyethylene glycol, natural starches, polyacrylamide, polymethacrylates, gums, protein, synthetic carbohydrates, and the like. These polymers also render the distinct area 22 of the matrix sheet 24 hydrophilic, so that the test area 22 of the sheet 24 wets much more readily than the remaining area of the "short fiber" paper. The surfactant may also contribute to the hydrophilicity of the area 22 when included in the composition.

As will be readily appreciated by those skilled in the art, the actual concentrations of the ingredients of the composition of the present invention may be varied, which will also result in varying the sensitivity of the test kit 20 and the intensity of the color which develops in a positive test. Therefore, although the specific concentrations and methods of mixing and applying the ingredients described in connection with the following specific examples provide a distinct color reaction when as little as 1.5 to 2.0 mg hemoglobin per 100 ml is present in the test solution, the examples should be considered exemplary rather than limiting in nature.

EXAMPLES

1. Two-Step Organic Application Process

A first reagent solution (hereinafter SOLUTION I) of one liter (1.0 L) final volume is prepared by admixing approximately 5 to 17 mg of ascorbic acid, approximately 3.18 g of alkylphenoxypolyethoxyethanol, approximately 1.0 g of urea peroxide, approximately 50–200 g of polyvinylpyrrolidone polymer, and 2 moles of citrate buffer with sufficient water to provide a final volume of 1.0 L. The citrate buffer is first prepared in an aqueous solution of smaller volume than 1.0 L, by adding sufficient potassium hydroxide (KOH) to two mols (384.42 g) of citric acid to adjust the pH to approximately 4.8. The surfactant alkylphenoxypolyethoxyethanol is also known under the tradename TRITON X-100, and the urea peroxide is also known under the tradename ORTIZONE.

A second reagent solution (hereinafter SOLUTION II) of one liter (1.0 L) final volume is prepared by admixing 400 ml of acetone, 55 g of $\alpha,\alpha'$-dimethylbenzoylperoxide, 25 g of 6-methoxyquinoline, 18 g of 3,3',5,5'-tetramethylbenzidine with 300 ml of an isopropanol solution already containing approximately 60% (by weight) of polyvinyl pyrrolidone. More acetone is then added to make up the 1.0 L volume.

Approximately 0.04 ml of the first solution (SOLUTION I) is then film coated to the distinct area 22 configured in the shape of a + sign substantially in the center of an approximately 3.25"×3.25" inch square of paper, and the area 22 containing the first solution is quickly dried, for example, by blowing heated air thereon. Then another film coat of the second solution (SOLUTION II) of approximately 0.04 ml volume is applied to the area 22 and the area 22 is dried again. The resulting test kit 20 thus contains the above-noted specific ingredients in the following amounts:

| | |
|---|---|
| ascorbic acid | 0.2–0.7 μg |
| alkylphenoxypolyethoxyethanol | 0.13 mg |
| urea peroxide | 0.04–4.0 mg |
| Polyvinylpyrrolidone polymer | 24 mg |
| citrate buffer | 0.08 mM |
| $\alpha,\alpha'$-dimethylbenzoylperoxide | 2.2 mg |
| 6-methoxyquinoline | 2.8 mg |
| 3,3',5,5'-tetramethylbenzidine | 0.72 mg |

The chemical composition, which contains the above-noted specific reagents, or their equivalents, can be film coated to the matrix of the paper sheet 24 in many ways. For example, microencapsulation can be used. However, the preferred method for film coating the chemical composition is by a printing technique which is best described with reference to FIGS. 5 and 6.

In accordance with this preferred technique, a continuous ribbon 26 of suitable paper (approximately 3.25" wide and 0.00125" thick, is passed through an apparatus having appropriate rolls and three (3) printing stations. At the first printing station, schematically designated as 28, SOLUTION I (as defined in the above-described Specific Example) is applied as a thin film to the paper in successive, repetitive steps in the configuration of the + sign, so that one imprint of approximately 0.04 ml of SOLUTION I is deposited on each (approximately 3.25" long) section of the ribbon 26. After having passed the first printing station 28, the continuously moving ribbon 26 is dried by hot air, and is fed into the second printing station 30 where approximately 0.04 ml of SOLUTION II is printed, superimposed on SOLUTION I. After another step of drying, the ribbon 26 proceeds into a third printing station 32, where such indicia 34, as desired, are printed on the ribbon 26 outside of the area 22 containing the chemical compositions. The indicia 34 may comprise printed directions, or other information pertaining to the test.

Figure 7:
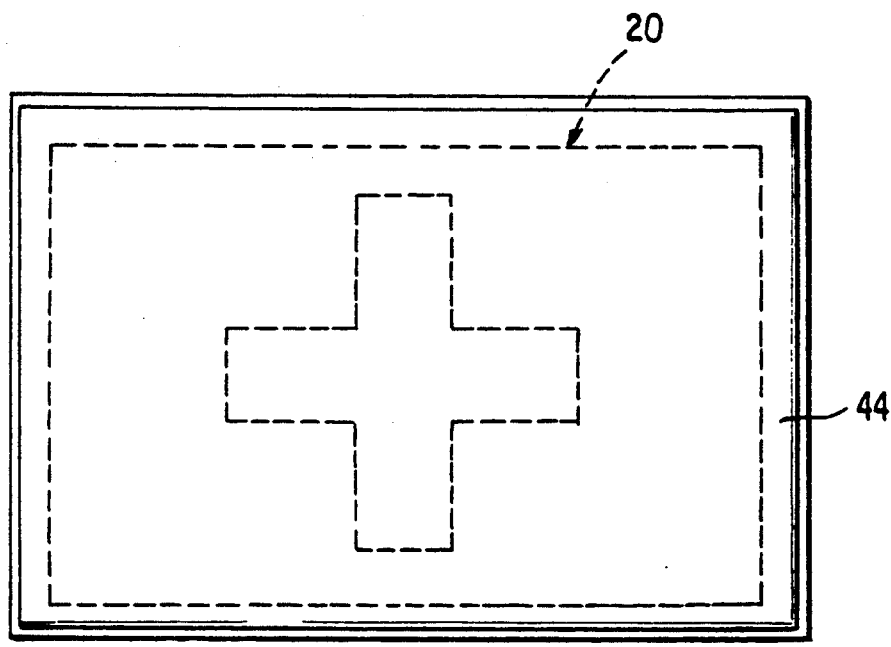
FIG. 7 is a schematic top view of a preferred embodiment of the inventive test kit in which a hermetically sealed envelope encloses the test kit of FIG. 3 (shown in phantom)
Figure 8:
FIG. 8 is an elevational side view of FIG. 7.

After printing, the ribbon 26 may be cut into individual 3.25"×3.25" pieces and put into an enclosure 44 shown in FIGS. 7 and 8, which is a substantially air, moisture, and light proof packaging envelope so as to provide the individual test kits 20 in a hermetically sealed envelope 44. In this regard, it is noted that the polymer which immobilizes and contains the reagents coated in polymer films prevents the reagents from reacting with one another during shipping and storage of the test kits. Nevertheless, long term storage is possible only when the test kit 20 is substantially hermetically sealed against atmospheric oxygen, moisture, and light.

Figure 5:
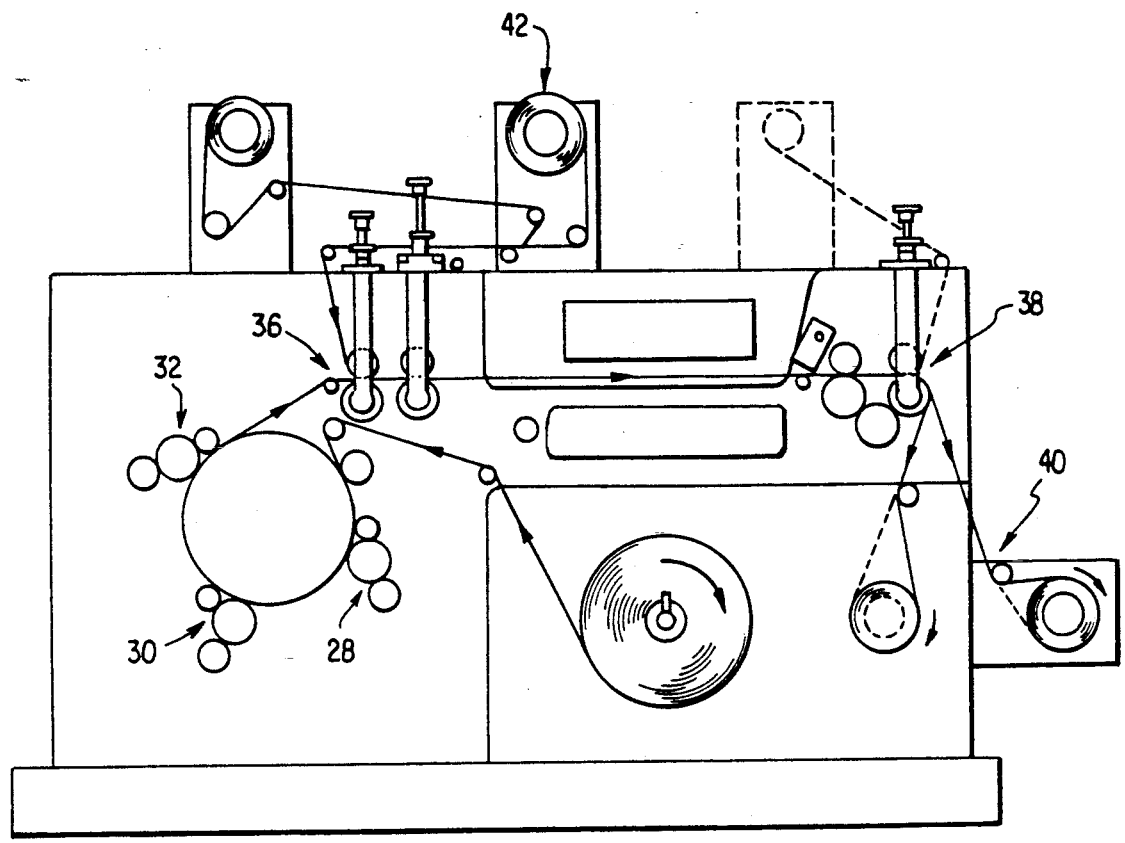
FIG. 5 is a view schematically showing a printing process whereby the preferred embodiment of the test kit of the present invention is manufactured.
Figure 6:
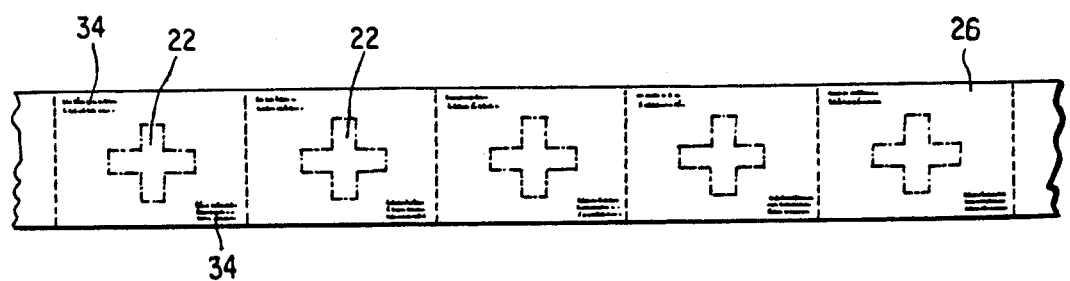
FIG. 6 is a schematic top view of an intermediate in the process of manufacturing the preferred embodiment of the test kit of the present invention.

The printing station, schematically shown on FIG. 5, includes several substations, which, per se, are known in the art, such as a web length adjusting substation 36, waste winder substation 38, rewinder substation 40, and cutter substation 42. Detailed description of these substations is not considered necessary to explain and describe the present invention.

One-Step Application Process

The test kit of the present invention may also be prepared by a single solution one-step application process. In this process the oxidizing agent, chromogen and water soluble polymer are dissolved in an organic solvent having a dielectric constant less than water. Specific example include N,N-diemethylformamide, dioxane, DMSO and acetonitrile. An organic acid which is soluble in the organic solvent is also added. Examples include malic, glutaric and fumeric acid. Complexing agents such as 6-methoxyquinoline and/or EDTA may also be included to modulate the color response.

In a specific example of the one-step process, a homogeneous solution having an organic reagent base is prepared having a final volume of one liter by admixing approximate quantities of N,N-dimethylformamide 94.4 g, polyvinylpyrrolidone approximately 336 g, 2-propanol approximately 443 g, $\alpha,\alpha'$-dimethylbenzoylperoxide 42 g, L-malic acid approximately 5.2 g, 6-methoxyquinoline approximately 17.5 g, 3,3'-5,5'-tetramethylbenzidine approximately 12.6 g. Approximately 0.04 ml of this solution is film coated to the distinct area 22 configured in the shape of a + sign in substantially the same manner as set forth in the two-step application process of example 1, except that since all the components are now present in a single solution, station 30 is no longer necessary.

The resulting test kit thus contains the above noted specified ingredients in the following amounts:

| | | |
|---|---|---|
| N,N-Dimethylformamide | 3.78 | mg |
| $\alpha,\alpha'$-Diethylbenzoylperoxide | 1.68 | mg |
| 3,3',5,5'-tetramethylbenzidine | 0.48 | mg |
| L-malic acid | 0.21 | mg |
| 2-propanol | 17.72 | mg |
| 6-methoxyquinoline | 0.7 | mg |
| polyvinylpyrrolidone | 13.44 | mg |

It will be readily understood by those skilled in the art that not only can the specific ingredients be changed within the scope of the present invention, but the process of preparing the solutions which contain the above-listed ingredients, as well as the specific ratios and weights of the ingredient, can also be changed within certain limits, by those skilled in the art, without departing from the scope of the present invention. However, it is an essential feature of the present invention that the several ingredients are film coated and stabilized in the water soluble polymer contained in the matrix of the test kit.

The following tables provide approximate limits of the same ingredients which were given in connection with the above-described examples.

Two-Step Application

| -continued | |
|---|---|
| ascorbic acid | 0.2–100 µg |
| alkylphenoxypolyethoxyethanol | .04–1.2 mg |
| urea peroxide | .01–4.0 mg |
| Polyvinylperolidone polymer | 8.0–30 mg |
| citrate buffer | .04–.10 mM |
| $\alpha,\alpha'$-dimethylbenzoylperoxide | 1.0–3.0 mg |
| 6-methoxyquinoline | 0.5–2.0 mg |
| 3,3',5,5'-tetramethylbenzidine | 0.4–1.0 mg |
| One-Step Application | |
| N,N-Dimethylformamide | 0.0–25 mg |
| 2-propanol | 0.0–30 mg |
| polyvinylpyrrolidone polymer | 6–30 mg |
| L-malic acid | 0.1–0.6 mg |
| $\alpha,\alpha'$-dimethylbenzoylperoxide | 1.0–3.0 mg |
| 6-methoxyquinoline | 0.5–2.0 mg |
| 3,3',5,5'-tetramethylbenzidine | .25–1.0 mg |
| urea peroxide | 0.01–4.0 mg |
| ascorbic acid | 0.2–100 µg |

It will also be readily understood by those skilled in the art that the distinct area 22, wherein the above-described chemical composition is applied to the matrix or paper sheet 24, can be varied in configuration and size. More than one distinct area having the composition may exist on the sheet 24, or the entire sheet 24 may be film coated with the chemical composition.

Best Mode of Using the Test Kit of the Present Invention

The test kit 20 of the present invention is suitable for detecting occult blood in various types of human and animal waste products, such as urine, stool, vomit, saliva, or breath. Where the waste product is itself an aqueous solution, such as urine, vomit, saliva, or the moisture in the breath of a human or animal, the solution can be applied directly to the test kit in order to detect the presence of occult blood in the sample. This is particularly important in the examination or evaluation of race horses which may bleed internally due to embolisms in their lungs. The blood will then be carried in the horse's breath or saliva to the animal's nose and mouth. The test kit 20 of the present invention can be placed at the horse's mouth or nose and will give a positive reading if there is blood in the animal's breath.

The primary application of the test kit 20 of the present invention is, however, for testing for occult blood in human stool or urine. Therefore, the use of the test kit 20 is described herein primarily in connection with the latter application.

Thus, in accordance with the test kit's recommended use, the individual, who anticipates performing the test, should preferably abstain for a day or two from consuming large amounts of red meat and certain vegetable substances (such a horseradish) which contain pseudo peroxidase enzyme activity. In order to perform the test, it is best to drop a freshly opened test kit 20 into a freshly flushed toilet bowl (not shown). A negative reaction (no color development) should follow, indicating that the toilet is suitable for performing the test. After the individual's stool or urine, or both (depending on the purpose of the test) are deposited in the toilet bowl, another freshly opened test kit 20 is dropped in the bowl. Development of a blue color within the +sign-shaped area 22 of the kit 20, in approximately 15 to 120 seconds, indicates the presence of blood in the urine or stool specimen. Individuals whose test is positive are advised to consult a physician at the earliest opportunity.

The test kit 20 of the present invention has sufficient sensitivity to provide meaningful test results, with the occurrence of false negative and false positive results being minimized, and a relatively low level of interference by external factors, such as the individual's diet or medication taken by the individual.

It will be readily recognized by those skilled in the art that the blue color, which indicates a positive result in the herein described test kit, is characteristic of the dye formed from 3,3',5,5'-tetramethylbenzidine contained as a chromogen in the specific example of the test kit of the present invention. In alternative embodiments, other chromogens may be employed, giving rise to different colors as an indication of the positive nature of the test. Inasmuch as several further modifications of the above-described invention may become readily apparent to those skilled in the art in light of the foregoing disclosure, the scope of the present invention should be interpreted solely from the following claims.

What is claimed is:

1. A testing kit adapted for testing fluids containing biological samples for the presence of a biological substance having peroxidase-like activity, the testing kit comprising at least one test device consisting essentially of:
   a matrix which is water insoluble and which is in the form of a sheet comprised of fibers of cellulose; and
   a composition film coated on the matrix to define at least one test area and consisting essentially of:
   a. at least one oxygen donor reagent selected from the group consisting of urea hydroperoxide and $\alpha,\alpha'$-dimethylbenzoyl peroxide;
   b. a chromogen reagent which is 3, 3',5,5'-tetramethylbenzidine and which is capable of being oxidized by the at least one oxygen donor reagent in the presence of a biological substance having peroxidase-like activity to provide a visually observable change of color;
   c. a water-soluble polymer which is polyvinylpyrrolidone and which is present in an amount effective to stabilize the remaining ingredients of the composition and to substantially prevent a premature change of color, the amount ranging between 38 to 50% by weight of the total composition;
   d. at least one surface active agent;
   e. at least one reducing agent, and
   f. a buffer having a pH ranging from approximately 4 to 6,
   wherein the chromogen reagent, the at least one oxygen donor reagent, the at least one surface active agent, the at least one reducing agent, and the buffer are coated by the water-soluble polymer so as to be contained therein and immobilized thereby.

2. The testing kit according to claim 1, wherein the composition contains approximately 0.4–1.0 mg of 3,3',5,5'-tetramethylbenzidine.

3. The testing kit according to claim 1, wherein the composition contains approximately 1.0–3.0 mg of $\alpha,\alpha'$-dimethylbenzoylperoxide and approximately 0.01–4.0 mg of urea hydroperoxide.

4. The testing kit according to claim 1, wherein the composition contains approximately 8.0–30 mg of polyvinylpyrrolidone.

5. The testing kit according to claim 1, wherein the at least one reducing agent comprises a substituted quinoline and ascorbic acid.

6. The testing kit according to claim 5, wherein the composition contains approximately 0.5–2.0 mg of 6-methoxyquinoline and approximately 0.2–100 $\mu$g of ascorbic acid.

7. The testing kit according to claim 1, further comprising an enclosure which is a hermetically sealed envelope which encloses the at least one test device and which is capable of being unsealed before testing for a biological substance having peroxidase-like activity.

8. The testing kit according to claim 1, wherein the at least one test area is a single test area configured as a plus sign.

9. The testing kit according to claim 1, wherein a visually observable change of color is obtained when the at least one test area is wetted with an aqueous solution containing at least about 1.5 mg of hemoglobin per 100 ml.

10. The testing kit according to claim 9, wherein a visually observable change of color is obtained when the at least test area is wetted with an aqueous solution containing at least about 2.0 mg of hemoglobin per 100 ml.

11. The testing kit according to claim 1, wherein a visually observable change of color is obtained when the test area is wetted with an aqueous solution including one of urine and stool in a period of time ranging from 15 to 120 seconds.

12. An anhydrous diagnostic composition for determining the presence in an aqueous solution of a substance having peroxidase-like activity, the anhydrous diagnostic composition comprising:
   a. at least one oxygen donor reagent;
   b. at least one chromogen reagent capable of being oxidized by the at least one donor reagent in the presence of a substance having peroxidase-like activity to provide a visually observable change of color; and
   c. at least one water-soluble polymer in which the at least one donor reagent and the at least one chromogen reagent are homogeneously dispersed, the at least one water-soluble polymer being present in an amount effective to stabilize the reagents and substantially prevent a premature change of color.

13. A testing kit for determining the presence in an aqueous solution of a substance having peroxidase-like activity, the testing kit comprising at least one test device comprised of:
   a carrier matrix; and
   a coating applied to at least at portion of the carrier matrix to define a test area and consisting essentially of a single composite comprising:
   a. at least one oxygen donor reagent;
   b. at least one chromogen reagent capable of being oxidized by the at least one donor reagent in the presence of a substance having peroxidase-like activity to provide a visually observable change of color; and
   c. at least one water-soluble polymer in which the at least one oxygen donor reagent and the at least one chromogen reagent are homogeneously dispersed, the at least one water-soluble polymer being present in an amount effective to stabilize the reagents and substantially prevent a premature change of color.

14. The testing kit according to claim 13, wherein the single composition further comprises at least one additive selected from the group consisting of a surface active agent, a reducing agent, a buffer having a pH ranging from about 4 to about 6, and mixtures thereof.

15. The testing kit according to claim 13, wherein the single composition is in a substantially anhydrous state and wherein the carrier matrix is substantially water insoluble.

16. The testing kit according to claim 13, wherein the carrier matrix is substantially water repellant, and wherein the test area contains an amount of at least one surface active agent effective to render the test area wettable by water.

17. A testing kit for determining the presence in an aqueous solution of a substance having peroxidase-like activity, the testing kit comprising at least one test device comprised of:

a. a carrier matrix;
b. a first coating applied to at least a portion of the carrier matrix to define a test area and being comprised of:
   at least one oxygen donor reagent; and
   at least one water-soluble polymer; and
c. a second coating superimposed onto the first coating and being comprised of:
   at least one oxygen donor reagent;
   at least one chromogen reagent capable of being oxidized by the at least one donor reagent in the presence of a substance having peroxidase-like activity to provide a visually observable change of color; and
   at least one water-soluble polymer,
   wherein the at least one water-soluble polymer is present in an amount effective to stabilize the reagents and substantially prevent a premature change of color.

18. The testing kit according to claim 17, wherein at least one of the first coating and the second coating comprises at least one additive selected from the group consisting of a surface active agent, a reducing agent, a buffer having a pH ranging from about 4 to about 6, and mixtures thereof.

19. The testing kit according to claim 17, wherein the first coating and the second coating are in substantially anhydrous states and wherein the carrier matrix is substantially water insoluble.

20. The testing kit according to claim 17, wherein the carrier matrix is substantially water repellant, and wherein the test area contains an amount of at least one surface active agent effective to render the test area wettable by water.

* * * * *